(12) United States Patent
Mliner et al.

(10) Patent No.: US 6,898,265 B1
(45) Date of Patent: May 24, 2005

(54) SCINTILLATOR ARRAYS FOR RADIATION DETECTORS AND METHODS OF MANUFACTURE

(75) Inventors: David Gerard Mliner, New Berlin, WI (US); Haochuan Jiang, Brookfield, WI (US); Richard Louis Hart, St. Johnsville, NY (US); Chang Wei, Niskayuna, NY (US); Jaime Andres Echeverry, Albany, NY (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/718,339

(22) Filed: Nov. 20, 2003

(51) Int. Cl.$^7$ ................................................ G21K 1/12
(52) U.S. Cl. .................... 378/19; 378/98.8; 250/370.11
(58) Field of Search ............ 378/19, 98.8; 250/363.01, 250/363.05, 363.08, 370.09, 370.11

(56) References Cited

U.S. PATENT DOCUMENTS

| | | |
|---|---|---|
| 3,749,920 A | 7/1973 | Sheldon |
| 4,069,355 A | 1/1978 | Lubowski et al. |
| 4,316,092 A | 2/1982 | Rabatin |
| 4,491,732 A | 1/1985 | Pritzkow et al. |
| 4,560,877 A | 12/1985 | Hoffman |
| 4,563,584 A | 1/1986 | Hoffman et al. |
| 4,720,426 A | 1/1988 | Englert et al. |
| 5,179,284 A * | 1/1993 | Kingsley et al. ........ 250/370.11 |
| 5,440,129 A | 8/1995 | Schmidt |
| 5,519,227 A | 5/1996 | Karellas |
| 5,585,280 A * | 12/1996 | Kwasnick et al. ............. 438/69 |
| 6,013,723 A | 1/2000 | Akao |
| 6,087,665 A | 7/2000 | Hoffman et al. |
| 6,173,031 B1 | 1/2001 | Hoffman et al. |
| 6,252,231 B1 | 6/2001 | Harootian |
| 6,348,693 B1 * | 2/2002 | Weisfield et al. ....... 250/370.11 |
| 6,448,566 B1 | 9/2002 | Riedner et al. |
| 6,479,824 B1 | 11/2002 | Hoffman |
| 2001/0045522 A1 * | 11/2001 | Homme et al. .......... 250/361 R |

* cited by examiner

Primary Examiner—Craig E. Church
Assistant Examiner—Irakli Kiknadze
(74) Attorney, Agent, or Firm—Carl B. Horton, Esq.; Armstrong Teasdale LLP

(57) ABSTRACT

A pixilated scintillator array for a radiation detector of an imaging system includes a plurality of scintillator pixels arranged side by side in an array. The scintillator pixels are separated from adjacent scintillator pixels by gaps. Each scintillator pixels includes a top surface, a plurality of side surfaces, and a first layer covering the top surface and the side surfaces of each scintillator pixel. The first layer is formed from a smoothing coating. A second layer formed from a reflective metal coating covers the first layer, and a third layer formed from a barrier coating covers the second layer.

24 Claims, 3 Drawing Sheets

SCINTILLATOR ARRAYS FOR RADIATION DETECTORS AND METHODS OF MANUFACTURE

BACKGROUND OF THE INVENTION

This invention relates generally to methods and apparatus for detecting radiation in CT imaging and other radiation imaging systems, and more particularly to scintillator arrays having increased reflectivity.

In at least some computed tomography (CT) imaging system configurations, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In some known CT systems, the x-ray source and the detector array are rotated with a gantry within the imaging plane and around the object to be imaged so that the angle at which the x-ray beam intersects the object constantly changes. X-ray sources typically include x-ray tubes, which emit the x-ray beam at a focal spot. X-ray detectors typically include a collimator for collimating x-ray beams received at the detector, a scintillator adjacent the collimator, and photodetectors adjacent the scintillator.

One or more rows of scintillator cells or scintillator pixels are provided in a detector array configured to acquire projection data from which one or more image slices of an object are reconstructed. One known detector array includes a two-dimensional array of scintillator cells, with each scintillator cell having an associated photodetector. An epoxy material is used to cast the scintillator cells into a block having specified dimensions for easier handling. To maximize reflectivity and to prevent cross-talk between adjacent detector cells, the cast reflector mixture includes a material having a high refractive index, such as $TiO_2$. Thus, light generated in the scintillating material by impinging x-rays is confined to the detector cell in which it is generated. However, neither the epoxy, the $TiO_2$, nor their mixture are particularly absorptive of x-rays. Thus, neither the photodetectors nor the cast reflector mixture itself is protected from damage caused by impinging x-rays.

In one known cast reflector mixture, a small amount of an oxide of chromium is also incorporated in the cast reflector mixture to further reduce cross-talk between cells. However, inclusion of this material reduces the efficiency of the detector, because the absorbed portion of the generated visible light is never detected by the photodetectors. Chrome is used to reduce the cross-talk by absorbing the light transmitting through the cast walls between pixels. This dopant significantly reduces the reflectivity from 98% to 82%, thus leading to very low light output. The introduction of chrome can reduce the light output by as much as 60% or higher. Also, the ability to reduce the cross-talk is limited. Newer CT applications require higher and higher resolution which means that the new design will require smaller pixels. The light output is further reduced as the pixel size become smaller because the relative opportunity of losing light on the surface is higher. The light output will be reduced by 20 to 25% when the pixel size is reduced by 50%. The low light output can cause image quality problems because of the low signal to noise ratio.

BRIEF DESCRIPTION OF THE INVENTION

In one aspect, a pixilated scintillator array for a radiation detector of an imaging system is provided. The scintillator array includes a plurality of scintillator pixels arranged side by side in an array. The scintillator pixels are separated from adjacent scintillator pixels by gaps. Each scintillator pixel includes a top surface, a plurality of side surfaces, and a first layer covering the top surface and the side surfaces of each scintillator pixel. The first layer is formed from a smoothing coating. A second layer formed from a reflective metal coating covers the first layer, and a third layer formed from a barrier coating covers the second layer.

In another aspect, a computed tomographic imaging system that includes a rotating gantry, a detector array on the rotating gantry, and a radiation source on the rotating gantry opposite the detector array and configured to direct a radiation beam through an object towards the detector array. The detector array includes a scintillator array optically coupled to a plurality of diodes. The scintillator array cincludes a plurality of scintillator pixels arranged side by side in an array. The scintillator pixels are separated from adjacent scintillator pixels by gaps. Each scintillator pixel includes a top surface, a plurality of side surfaces, and a first layer covering the top surface and the side surfaces of each scintillator pixel. The first layer is formed from a smoothing coating. A second layer formed from a reflective metal coating covers the first layer, and a third layer formed from a barrier coating covers the second layer.

In another aspect, a method of making a scintillator array is provided. The method includes providing a pixilated scintillator pack preform including a plurality of scintillator pixels arranged side by side in an array and separated by a gap, with each pixel having a top surface and a plurality of side surfaces. The method also includes applying a smoothing coating on the top surface and the side surface of each scintillator pixel to form a smoothing layer, applying a reflective metal coating on top of the smoothing layer to form a reflective metal layer, and applying a barrier coating on top of the reflective metal layer to form a barrier layer.

DETAILED DESCRIPTION OF THE INVENTION

A pixilated scintillator array for a radiation detector of an imaging system is described below in detail. The scintillator array includes a polymer smoothing coating on the top and side surfaces of the pixels of the scintillator array. The smoothing coating has a low refractive index of less than 1.5 and improves adhesion and reflectance of a reflective metal coating that is deposited on top of the smoothing coating on the top and side surfaces of the pixels of the array. A barrier coating is applied on top of the reflective metal coating and provides for protection of the reflective coating which increases the durability of the scintillator array. The design of the pixilated scintillator array provides for an increase in output of between about 50 percent to about 100 percent over current commercial scintillator arrays. The pixilated scintillator array is described below in relation to a computed tomography (CT) imaging system. However, the pixilated scintillator array can be used in other imaging systems, including imaging systems that utilize radiation sources other than an x-ray source, for example, a gamma ray source.

Figure 1:
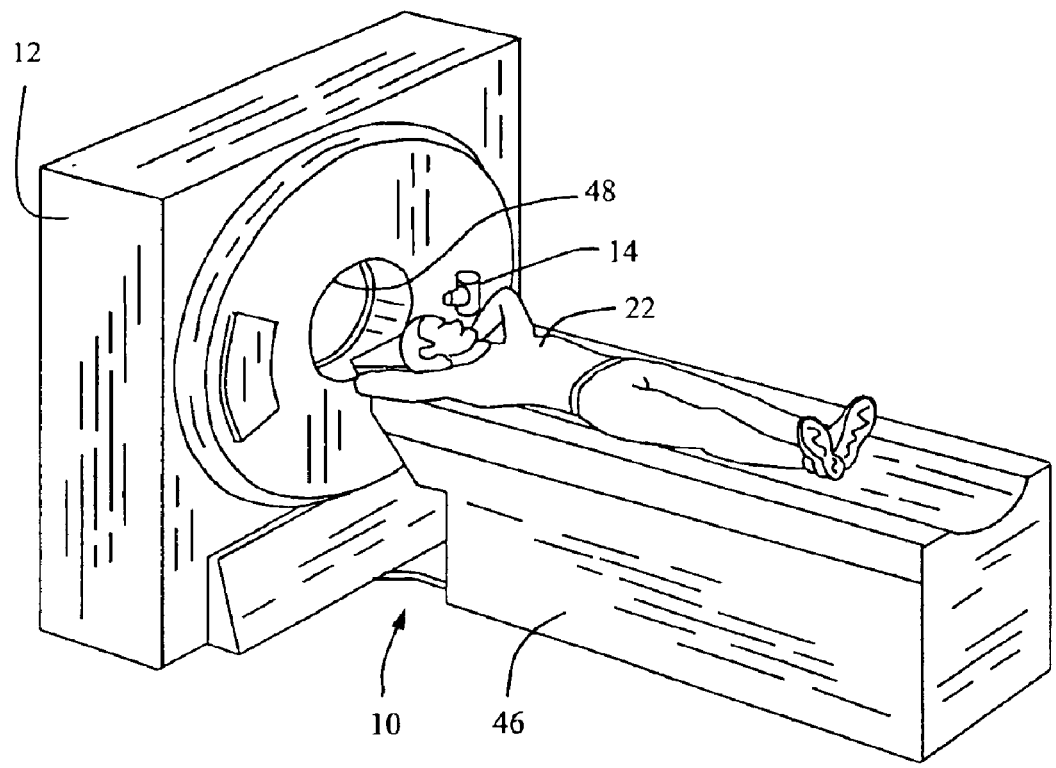
FIG. 1 is a pictorial view of a CT imaging system.
Figure 2:
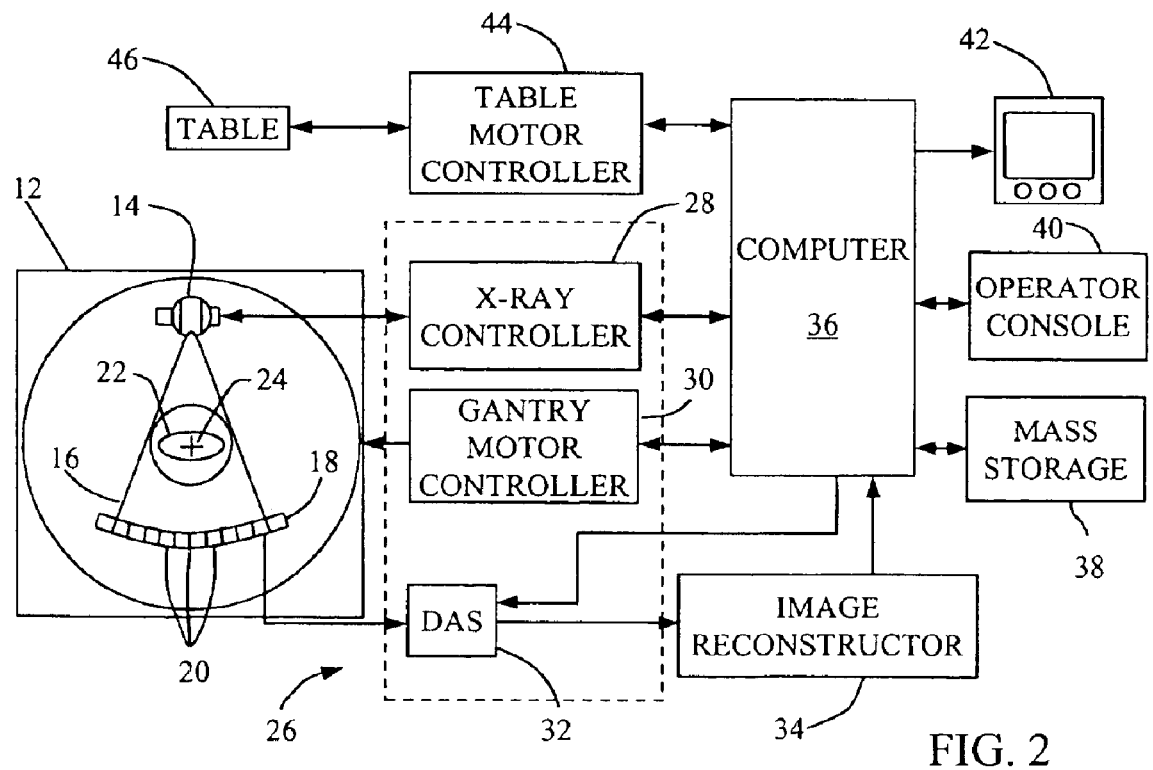
FIG. 2 is a block schematic diagram of the system illustrated in FIG. 1.

Turning now to the drawings, and referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object, such as a medical patient 22. Each detector element 20 produces an electrical signal that represents the intensity of an impinging x-ray beam and hence the attenuation of the beam as it passes through object or patient 22. During a scan to acquire x-ray projection data, gantry 12 and the components mounted thereon rotate about a center of rotation 24. In one embodiment, and as shown in FIG. 2, detector elements 20 are arranged in one row so that projection data corresponding to a single image slice is acquired during a scan. In another embodiment, detector elements 20 are arranged in a plurality of parallel rows, so that projection data corresponding to a plurality of parallel slices can be acquired simultaneously during a scan.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
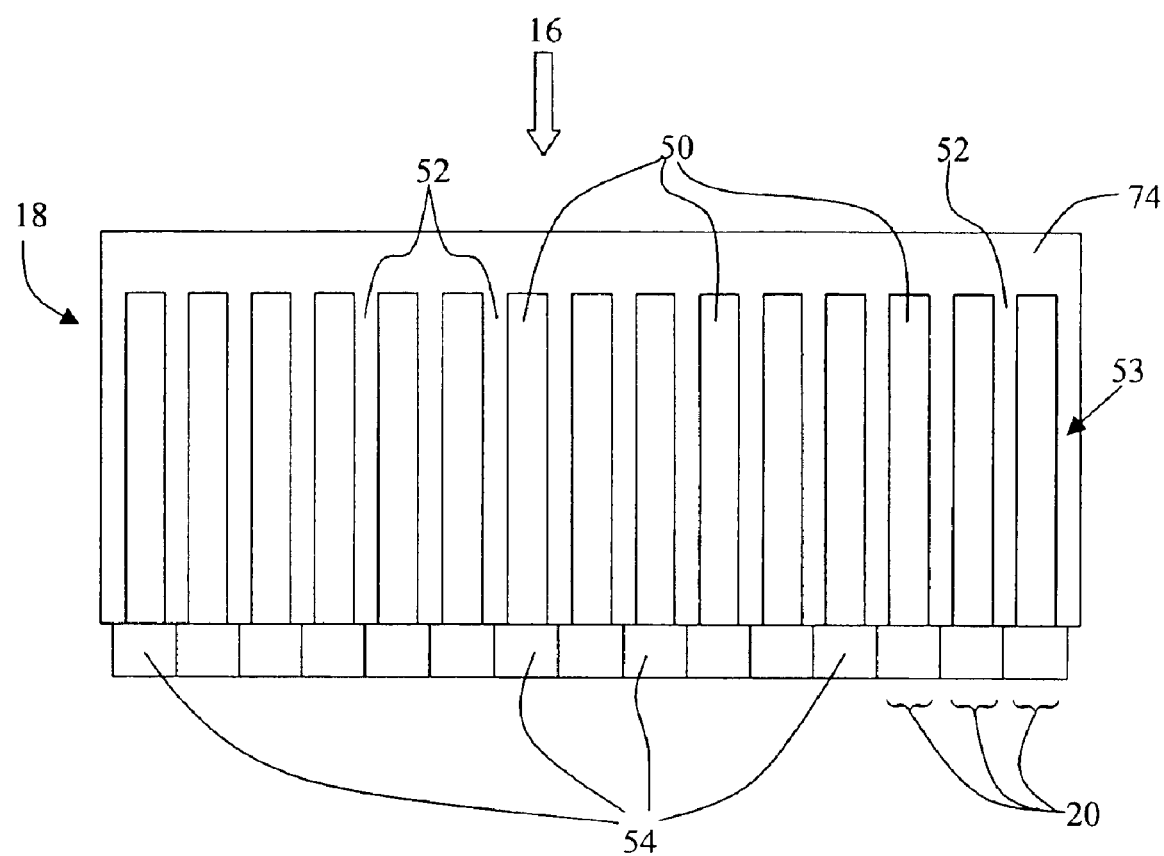
FIG. 3 is a sectional illustration of the detector array shown in FIG. 2.

As explained above, each detector element 20 of array 18 produces a separate electrical signal that is a measurement of the beam attenuation at the detector location. Particularly, and referring to FIG. 3, each x-ray detector element 20 includes a scintillator element 50, and sides of adjacent scintillator elements 50 are separated by non-scintillating gaps 52. Scintillator elements 50 are also referred to herein as scintillator pixels 50 and are arranged in an array 53. In addition, although FIG. 3 depicts a cross section through a row of detector elements 20, FIG. 3 is intended to be representative of both linear and two-dimensional (e.g., rectangular) arrays of detector elements 20. When struck by x-rays, scintillator elements 50 convert at least a portion of energy of the x-rays into light that can be detected by photo-detectors 54 positioned adjacent scintillator elements 50. Photodetectors 54 (for example, photodiodes or photocells) optically coupled to the backs of scintillator elements 50 generate electrical signals representative of the light output by scintillator elements 50. The attenuation measurements from all detector elements 20 in detector array 18 are acquired separately to produce a transmission profile.

Figure 4:
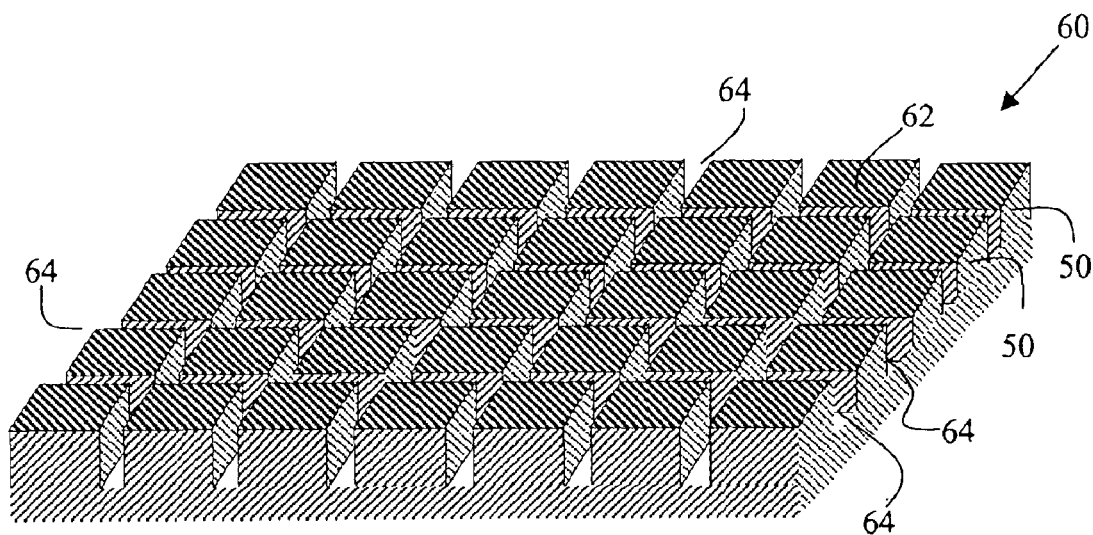
FIG. 4 is a perspective illustration of a pixilated scintillator pack preform.

FIG. 4 is a perspective illustration of a pixilated scintillator pack preform 60. In an exemplary embodiment, scintillator pack preform 60 is a two dimensional array of scintillator pixels 50. Each pixel 50 has a top surface 62 and a plurality of side surfaces 64. Preform 60 is formed by using geometric cutting methods such as OD saw dicing or wire saw dicing techniques to cut pixels 50 into a block scintillator material. Preform 60 can also be formed with other near net shape processes such as injection molding. Pixels 50 are temporarily held together by a portion 66 of scintillator material that is not cut. After the pixel coating processes described below, portion 66 is ground away and pixels 50 are coupled to photodetectors 54 (shown in FIG. 3).

Figure 5:
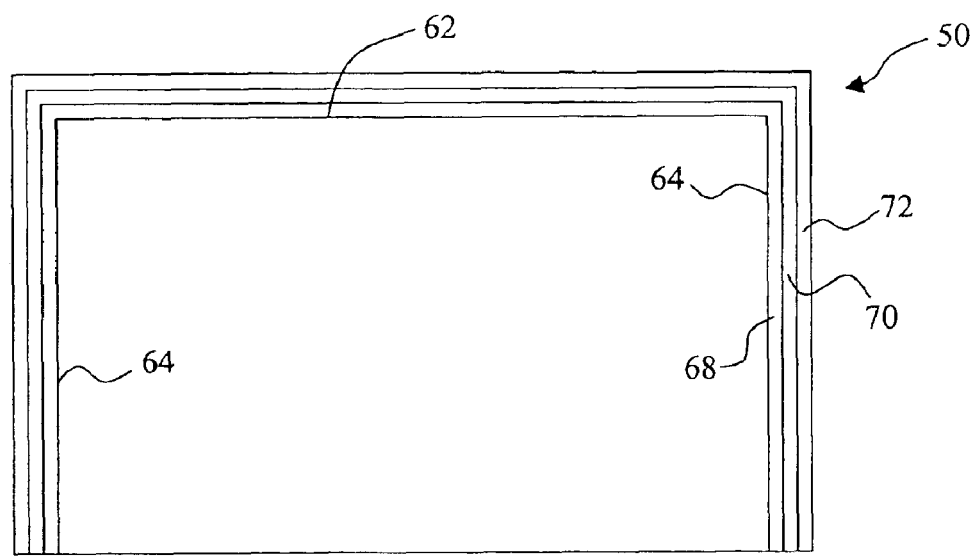
FIG. 5 is a section illustration of a scintillator pixel of scintillator pack preform shown in FIG. 4.

Referring also to FIG. 5, each scintillator pixel 50 includes a smoothing layer 68 covering top surface 62 and each side surface 64 of scintillator pixel 50. Smoothing layer 68 is formed from a smoothing coating material. The coating material that forms smoothing layer 68 has a refractive index of less than 1.5. The smoothing coating material is applied in one or more coats in sufficient quantity so that in one embodiment, the dry film thickness of the coating material, and thus, of smoothing layer 68 is about 0.5 micrometer ($\mu$m) to about 3.0 $\mu$m. In another embodiment, the thickness of smoothing layer 68 is about 1.0 $\mu$m to about 2.0 $\mu$m. The smoothing coating is applied by any suitable coating technique, for example, dip and spin coating. Suitable smoothing coating materials include, but are not limited to, silicone hard coatings, including UV curable silicone hard coatings, for example, UVHC8558 commercially available from General Electric Company, and styrene acrylate coatings.

A reflective metal layer 70 is formed on top of smoothing layer 68. Metal layer 70 is formed by depositing a metal coating on to top surface 62 and side surfaces 64 that have been previously coated with a smoothing coating that forms smoothing layer 68. Reflective metal layer 70 has a high reflective surface that is capable of reflecting greater than about 95 percent of the light produced by scintillator pixel 50 back from all incident angles to be detected by photodetector 54 (shown in FIG. 3). Any suitable metal coating can be used, for example, silver, gold, or aluminum. In the exemplary embodiment, a silver coating is used. In one embodiment, the metal coating is deposited to produce a metal layer 70 thickness of about 0.1 $\mu$m to about 3.0 $\mu$m. In another embodiment, the metal coating is deposited to produce a metal layer 70 thickness of about 0.5 $\mu$m to about 2.0 $\mu$m. A minimum thickness of about 0.1 $\mu$m is needed to achieve 0% transmission for low cross-talk and high reflectivity for high light output from scintillator pixels 50. The deposition of the metal coating can be done by any suitable method, for example, sputtering techniques (vacuum vapor deposition), chemical vapor deposition (CVD), plasma assisted CVD, or electroless coating techniques. It is important that a uniform thickness of the metal coating is deposited across all surfaces of scintillator pixels 50.

To protect reflective metal layer 70, a barrier layer 72 is formed by the deposition of a barrier coating material on top of metal layer 70. The barrier coating material is applied in one or more coats in sufficient quantity so that in one embodiment, the dry film thickness of the coating material, and thus, of barrier layer 72 is about 0.5 am to about 15.0 $\mu$m. In another embodiment, the thickness of barrier layer 72 is about 2.0 $\mu$m to about 10.0 $\mu$m. The barrier coating is applied by any suitable coating technique, for example, dip and spin coating. Suitable barrier coating materials include, but are not limited to, silicone hard coatings, including UV curable silicone hard coatings, for example, UVHC8558 commercially available from General Electric Company, and epoxy coatings, for example, EpoTek 301 commercially available from Epoxy Technology, Inc.

After smoothing layer 68, reflective metal layer 70 and barrier layer 72 have been formed on each scintillator pixel 50, an adhesive material 74 (shown in FIG. 3) containing, in one embodiment, about 15 weight percent to about 60 weight percent $TiO_2$ is cast into pack preform 60 to fill gaps 52. In another embodiment, adhesive material contains about 20 weight percent to about 50 weight percent $TiO_2$. It should be understood that the filler material of adhesive material 74 is not limited to $TiO_2$, and can, in other embodiments, include other high-Z oxide materials, for example, $Ta_2O_5$, $Bi_2O_3$, WO3, PbO, and $HfO_2$, and/or metal powders, for example, tungsten. Adhesive material 74 is a low viscosity radiation resistant epoxy that can be cured at room temperature or higher. After the epoxy material is cured, pack preform 60 is machined into its final dimensions.

To make a finished scintillator array 53, pixilated scintillator preform 60 is cleaned, for example with an acid cleaning solution, and then dried. A smoothing coating composition is applied to top surface 62 and side surfaces 64 of scintillator pixels 50. The deposited smoothing coating is cured to form smoothing layer 68. Next a reflective metal coating is applied on top of smoothing layer 68, covering all surfaces of pixels 50 to form reflective metal layer 70. Then a barrier coating is applied on top of metal layer 70 and cured to form barrier layer 72. Adhesive material 74 is then cast onto preform 60 filling all gaps 52 and covering all surfaces of scintillator pixels 50. Adhesive material is then cured and preform 60 is then machined to its final dimensions.

While the invention has been described in terms of various specific embodiments, those skilled in the art will recognize that the invention can be practiced with modification within the spirit and scope of the claims.

What is claimed is:

1. A pixilated scintillator array for a radiation detector of an imaging system, said scintillator array comprising:
   a plurality of scintillator pixels arranged side by side in an array, said scintillator pixels separated from adjacent scintillator pixels by gaps, each said scintillator pixel comprising:
   a top surface and a plurality of side surfaces;
   a first layer covering said top surface and said side surface of each said scintillator pixel, said first layer formed from a smoothing coating;
   a second layer covering said first layer, said second layer formed from a reflective metal coating; and
   a third layer covering said second layer, said third layer formed from a barrier coating.

2. A scintillator array in accordance with claim 1 wherein said reflective metal coating comprises at least one of silver, gold and aluminum.

3. A scintillator array in accordance with claim 1 wherein said smoothing coating has a refractive index less than 1.5.

4. A scintillator array in accordance with claim 1 wherein said first layer is about 0.5 $\mu$m to about 3.0 $\mu$m in thickness.

5. A scintillator array in accordance with claim 4 wherein said first layer is about 1.0 $\mu$m to about 2.0 $\mu$m in thickness.

6. A scintillator array in accordance with claim 1 wherein said second layer is about 0.1 $\mu$m to about 3.0 $\mu$m in thickness.

7. A scintillator array in accordance with claim 6 wherein said second layer is about 0.5 $\mu$m to about 2.0 $\mu$m in thickness.

8. A scintillator array in accordance with claim 1 wherein said third layer is about 0.5 $\mu$m to about 15.0 $\mu$m in thickness.

9. A scintillator array in accordance with claim 8 wherein said third layer is about 2.0 $\mu$m to about 10.0 $\mu$m in thickness.

10. A scintillator array in accordance with claim 1 further comprising an adhesive material filling said gaps between said scintillator pixels, said adhesive material comprising about 15 weight percent to about 60 weight percent of a filler material comprising at least one of $TiO_2$, $Ta_2O_5$, $Bi_2O_3$, WO3, PbO, $HfO_2$, and tungsten, the weight percent based on the total weight of the adhesive material.

11. A scintillator array in accordance with claim 10 wherein said adhesive material comprises about 20 weight percent to about 50 weight percent of the filler material, the weight percent based on the total weight of the adhesive material.

12. A computed tomographic imaging system comprising:
   a rotating gantry;
   a detector array on said rotating gantry; and
   a radiation source on said rotating gantry opposite said detector array and configured to direct a radiation beam through an object towards said detector array;
   said detector array comprising a scintillator array optically coupled to a plurality of diodes, said scintillator array comprising:
   a plurality of scintillator pixels arranged side by side in an array, said scintillator pixels separated from adjacent scintillator pixels by gaps, each said scintillator pixel comprising:
   a top surface and a plurality of side surfaces;
   a first layer covering said top surface and said side surface of each said scintillator pixel, said first layer formed from a smoothing coating;
   a second layer covering said first layer, said second layer formed from a reflective metal coating; and
   a third layer covering said second layer, said third layer formed from a barrier coating.

13. An imaging system in accordance with claim 12 wherein said reflective metal coating comprises at least one of silver, gold and aluminum.

14. An imaging system in accordance with claim 12 wherein said smoothing coating has a refractive index less than 1.5.

15. An imaging system in accordance with claim 12 wherein said first layer is about 1.0 $\mu$m to about 2.0 $\mu$m in thickness.

16. An imaging system in accordance with claim 12 wherein said second layer is about 0.5 $\mu$m to about 2.0 $\mu$m in thickness.

17. An imaging system in accordance with claim 12 wherein said third layer is about 2.0 μm to about 10.0 μm in thickness.

18. An imaging system in accordance with claim 12 wherein said scintillator array further comprises an adhesive material filling said gaps between said scintillator pixels, said adhesive material comprising about 20 weight percent to about 50 weight percent of a filler material comprising at least one of $TiO_2$, $Ta_2O_5$, $Bi_2O_3$, WO3, PbO, $HfO_2$, and tungsten, the weight percent based on the total weight of the adhesive material.

19. A method of making a scintillator array comprising:
   providing a pixilated scintillator pack preform comprising a plurality of scintillator pixels arranged side by side in an array and separated by a gap, each pixel having a top surface and a plurality of side surfaces;
   applying a smoothing coating on the top surface and the side surface of each scintillator pixel to form a smoothing layer;
   applying a reflective metal coating on top of the smoothing layer to form a reflective metal layer; and
   applying a barrier coating on top of the reflective metal layer to form a barrier layer.

20. A method in accordance with claim 19 wherein applying a smoothing coating comprises applying a smoothing coating on the top surface and the side surface of each scintillator pixel to form a smoothing layer of about 1.0 μm to about 2.0 μm in thickness.

21. A method in accordance with claim 19 wherein applying a reflective metal coating comprises applying a reflective metal coating on top of the smoothing layer to form a reflective metal layer of about 0.5 μm to about 2.0 μm in thickness.

22. A method in accordance with claim 19 wherein applying a barrier coating comprises applying a barrier coating on top of the reflective metal layer to form a barrier layer of about 2.0 μm to about 10.0 μm in thickness.

23. A method in accordance with claim 19 wherein the smoothing coating has a refractive index less than 1.5.

24. A method in accordance with claim 19 further comprising casting an adhesive material on top of the barrier coating and filling the gaps between the scintillator pixels, the adhesive material comprising about 15 weight percent to about 60 weight percent of a filler material comprising at least one of $TiO_2$, $Ta_2O_5$, $Bi_2O_3$, WO3, PbO, $HfO_2$, and tungsten, the weight percent based on the total weight of the abrasive material.

* * * * *